United States Patent
Wood et al.

[11] Patent Number: 5,746,755
[45] Date of Patent: May 5, 1998

[54] METHOD AND DEVICE FOR PROVIDING HEMOSTASIS AT VASCULAR PENETRATION SITES

[75] Inventors: Timothy J. Wood, Santa Clara; Bernard H. Andreas, Fremont, both of Calif.

[73] Assignee: Perclose, Inc., Menlo Park, Calif.

[21] Appl. No.: 559,254

[22] Filed: Nov. 15, 1995

Related U.S. Application Data

[63] Continuation of Ser. No. 252,483, Jun. 1, 1994, abandoned.
[51] Int. Cl.$^6$ .................................................. A61B 17/00
[52] U.S. Cl. ........................ 606/148; 606/144; 606/213
[58] Field of Search ............................... 606/144, 148, 606/151, 157, 159, 194, 213–216

[56] References Cited

U.S. PATENT DOCUMENTS

| | | |
|---|---|---|
| 1,574,362 | 2/1926 | Callahan . |
| 1,940,351 | 12/1933 | Howard . |
| 2,131,321 | 9/1938 | Hart . |
| 2,595,086 | 4/1952 | Larzelere . |
| 4,610,248 | 9/1986 | Rosenberg .................... 606/148 |
| 4,655,211 | 4/1987 | Sakamoto et al. ............ 606/213 X |
| 4,744,364 | 5/1988 | Kensey . |
| 4,803,984 | 2/1989 | Narayanan et al. . |
| 4,852,568 | 8/1989 | Kensey . |
| 4,890,612 | 1/1990 | Kensey . |
| 4,929,246 | 5/1990 | Sinofsky . |
| 5,021,059 | 6/1991 | Kensey et al. ................. 606/213 |
| 5,061,274 | 10/1991 | Kensey . |
| 5,108,421 | 4/1992 | Fowler . |
| 5,129,882 | 7/1992 | Weldon et al. . |
| 5,163,946 | 11/1992 | Li .................................. 606/148 |
| 5,176,691 | 1/1993 | Pierce ............................ 606/148 |
| 5,192,302 | 3/1993 | Kensey et al. . |
| 5,201,744 | 4/1993 | Jones . |
| 5,222,974 | 6/1993 | Kensey et al. ................. 606/213 |
| 5,250,054 | 10/1993 | Li . |
| 5,254,113 | 10/1993 | Wilk .............................. 606/213 |
| 5,275,616 | 1/1994 | Fowler .......................... 606/213 |
| 5,290,310 | 3/1994 | Makower et al. .............. 606/213 |
| 5,292,327 | 3/1994 | Dodd et al. ................... 606/148 |
| 5,292,332 | 3/1994 | Lee ................................ 606/213 |
| 5,320,629 | 6/1994 | Noda et al. ................... 606/148 |
| 5,417,699 | 5/1995 | Kleine t al. ................... 606/144 |
| 5,419,765 | 5/1995 | Weldon et al. ............... 606/213 |
| 5,507,744 | 4/1996 | Tay et al. ...................... 606/50 |

FOREIGN PATENT DOCUMENTS

| | | | |
|---|---|---|---|
| 543499 | 5/1993 | European Pat. Off. ............... | 606/213 |

OTHER PUBLICATIONS

Ernst, J. et al., "Immediate Sealing or Arterial Puncture Sites After Catheterization and PTCA Using a Vascular Hemostasis Device With Collagen: An International Registry." (ndated).

Merino, A. et al., "A Vascular Hemostasis Device for Percuitaneous Interventional Procedures," Mount Sinai Medical Center, N.Y. (undated).

"The Hemostatic Puncture Closure Device," Kensey Nash Corporation. (undated).

*Primary Examiner*—Michael Peffley
*Attorney, Agent, or Firm*—Townsend and Townsend and Crew LLP

[57] ABSTRACT

A device for providing or enhancing hemostasis at a vascular puncture site disposed at the distal end of a tissue tract comprises a shaft having a non-compliant surface at its distal end. The non-compliant surface is oriented at an angle which allows it to lie flat over tissue puncture when the tissue tract is oriented obliquely, e.g., as the result of the Seldinger catheter introduction technique. The device may be used by itself or in combination with suturing of the vascular puncture, where the device enhances hemostasis and prevents blood leakage through the primary suture closure.

32 Claims, 8 Drawing Sheets

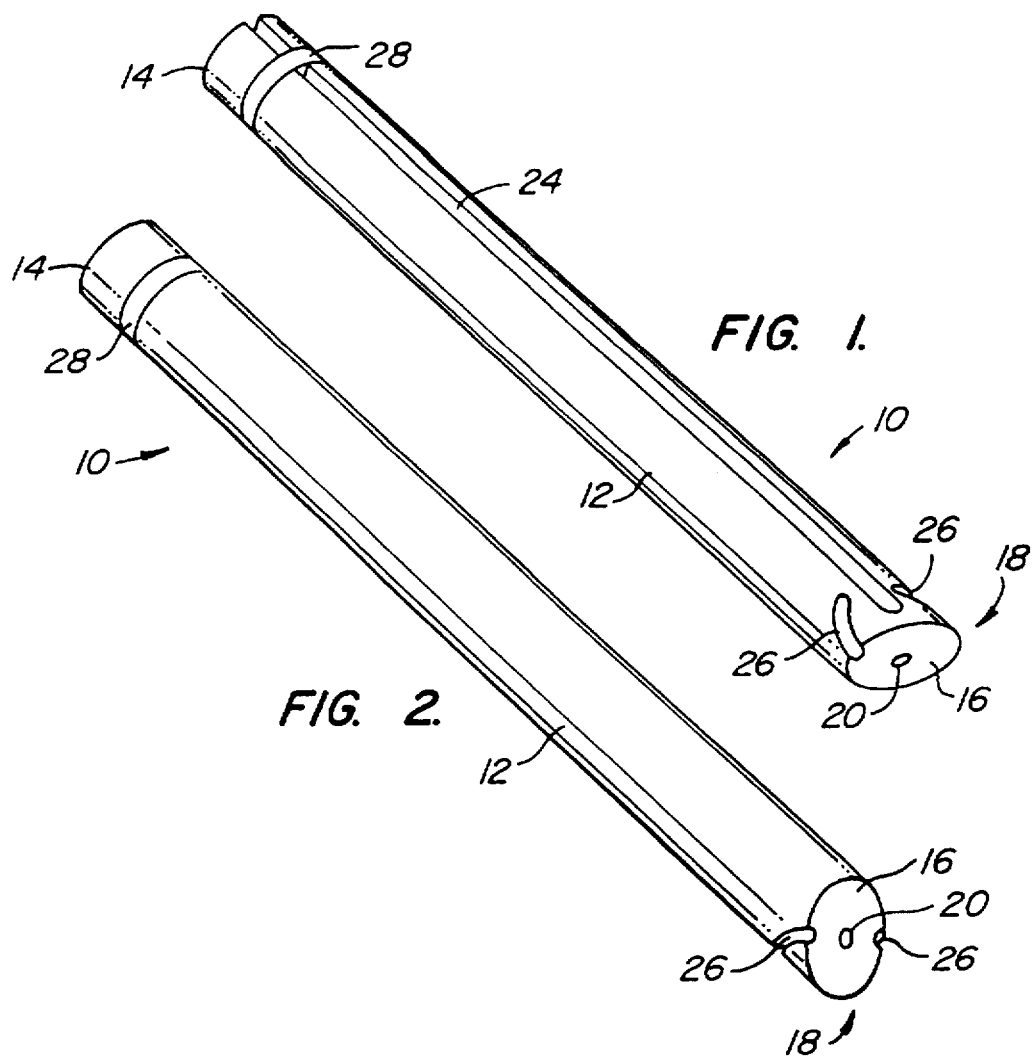
FIG. 1.
FIG. 2.
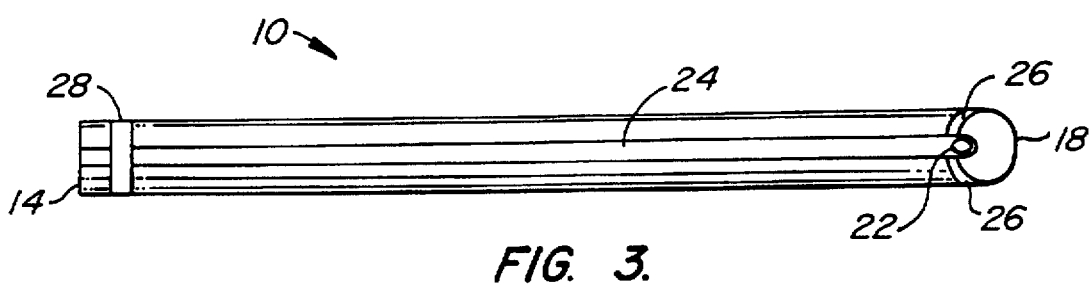
FIG. 3.
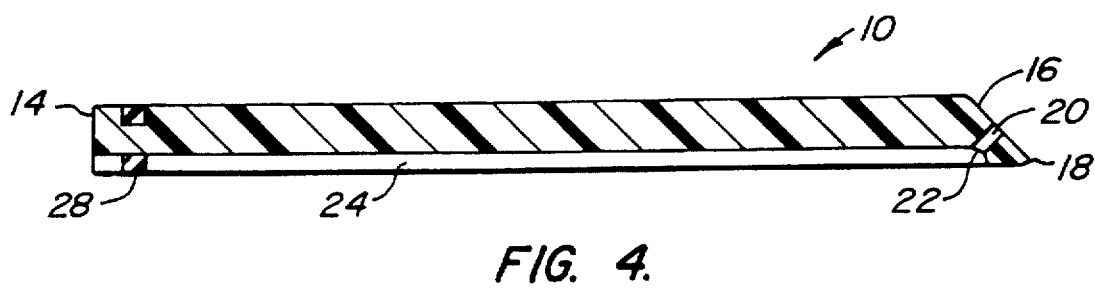
FIG. 4.

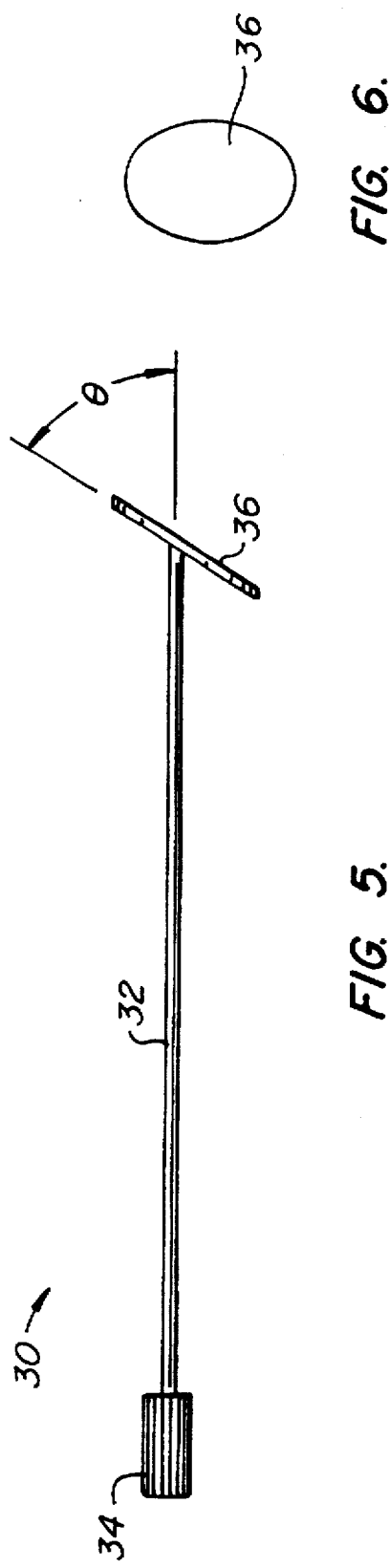

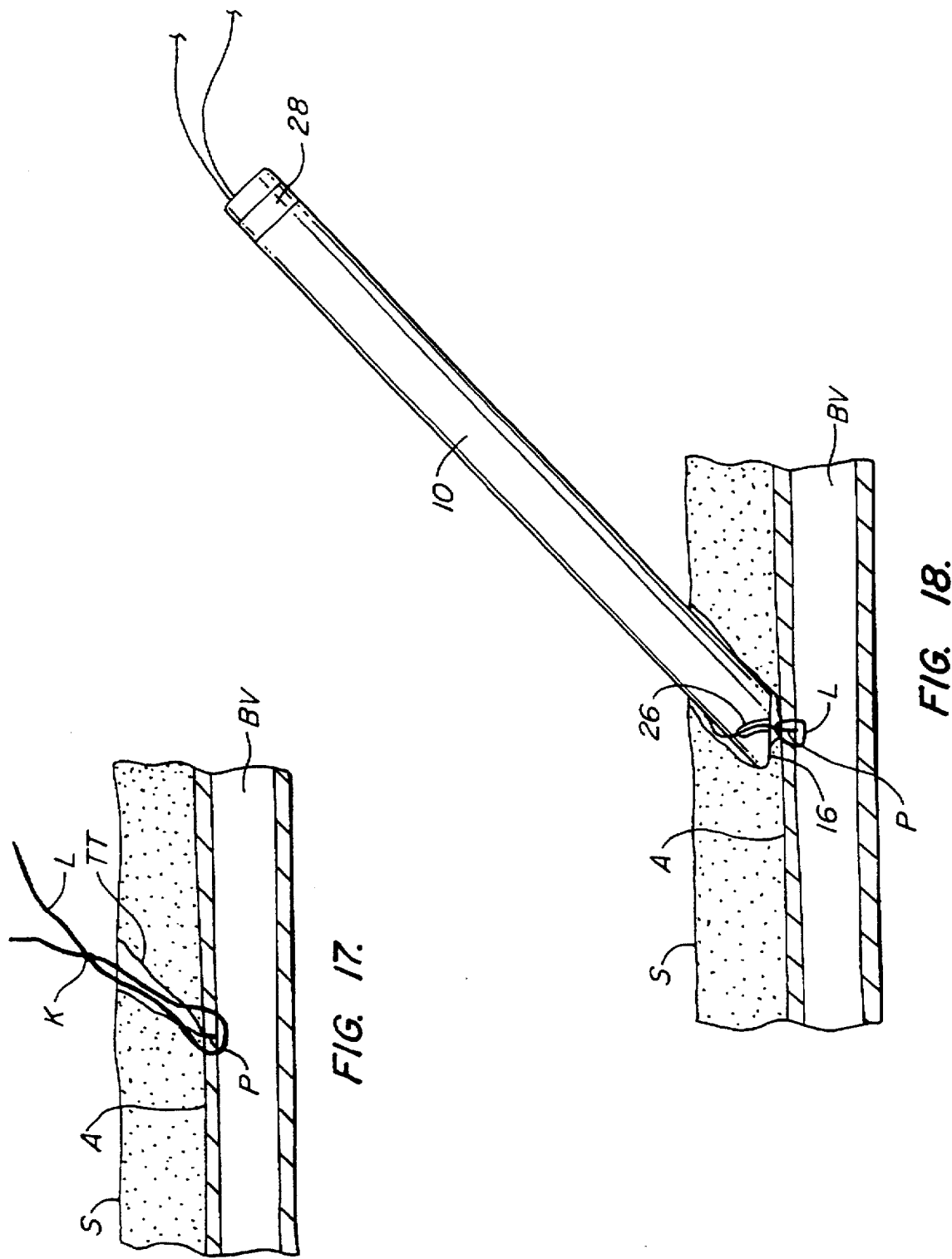

METHOD AND DEVICE FOR PROVIDING HEMOSTASIS AT VASCULAR PENETRATION SITES

This is a Continuation of U.S. application Ser. No. 08/252,483, filed Jun. 1, 1994 now abandoned.

BACKGROUND OF THE INVENTION

1. Field of the Invention

The present invention relates generally to methods and apparatus for occluding vascular punctures. More particularly, the present invention relates to a device which may be introduced through a tissue tract to apply pressure directly over the adventitial surface of a blood vessel wall in the region of the vascular puncture.

Coronary and other vascular catheters are usually introduced to a patient's vasculature by the Seldinger technique. A small gauge needle is introduced through the skin to a target blood vessel, such as the femoral artery in the region of the patient's groin for coronary procedures. The needle forms a puncture through the blood vessel wall at the distal end of a tract through the overlying tissue. A guide wire is then introduced through the needle, and the needle withdrawn over the guide wire. An introducer sheath is next introduced over the guide wire, and the sheath and guide wire are left in place to provide access during subsequent procedure(s). Exemplary procedures include diagnostic procedures such as angiography, ultrasonic imaging, and the like, and interventional procedures, such as angioplasty, atherectomy, stent placement, laser ablation, graft placement, and the like. After the procedures are completed, the catheters, guide wire, and introducer sheath are removed, and it is necessary to close the vascular puncture to provide hemostasis (i.e., stop blood loss) and allow healing.

The most common technique for providing "hemostasis" is to apply pressure on the patient's skin in the region of the tissue tract and vascular puncture. Pressure can be applied manually or through the use of mechanical clamps and other pressure-applying devices. While effective in most cases, the application of external pressure to the patient's skin suffers from a number of disadvantages. When applied manually, the procedure is time-consuming, frequently requiring the presence of a nurse for one-half hour or more. For both manual and mechanical pressure application, the procedure is uncomfortable for the patient and frequently requires the administration of analgesics to be tolerable. Moreover, the application of excessive pressure can sometimes occlude the underlying artery, resulting in ischemia and/or thrombosis. Even after hemostasis has apparently been achieved, the patient must remain still and under observation for hours to assure that the bleeding remains stopped. Renewed bleeding through the tissue tract is not uncommon and can result in hematoma, pseudoaneurisms, and arteriovenous fistulas. Such complications may require blood transfusion, surgical intervention, or other corrective procedures. The risk of these complications increases with the use of larger sheath sizes, which are frequently necessary in interventional procedures, and when the patient is anticoagulated.

To overcome these problems, several groups have proposed the use of bioabsorbable plugs and fasteners to stop bleeding. Generally, these approaches rely on placing a bioabsorbable material, such as collagen, at the adventitial blood vessel wall over the puncture site. While potentially effective, the use of collagen plugs also suffers from certain problems. It can be difficult to properly locate the plug at the interface between the tissue and adventitial surface of the blood vessel. To help in such positioning, some systems rely on placement of a fastener within the blood vessel lumen to locate and anchor the collagen plug. The use of such fasteners, however, can cause other complications, such as thrombosis, embolization, and the like.

A more effective approach has been proposed in copending application Ser. No. 07/989,611 now U.S. Pat. No. 5,417,699; Ser. No. 08/148,809 now U.S. Pat. No. 5,527,325; and PCT/US93/11864. A suture applying device is introduced through the tissue tract with its distal end located at the vascular puncture. One or more needles on the device are used to draw a suture through the blood vessel wall on opposite sides of the puncture, and the suture is secured directly over the adventitial surface of the blood vessel wall to provide highly reliable closure. While a significant improvement over the use of manual pressure, clamps, and collagen plugs, in rare cases there can still be blood leakage through the sutured vascular puncture, particularly when the patient has been heavily treated with anticoagulants. Moreover, it is desirable to be able to tightly cinch the suture loops which are formed to assure complete closure of the puncture.

For these reasons, it would be desirable to provide improved methods and devices for effecting and enhancing hemostasis at vascular puncture sites after vascular catheterization procedures. In particular, it would be desirable to provide improved methods and devices for stopping bleeding at vascular puncture sites which have been sutured as a primary means of closure. It would be further desirable if such methods and devices could also serve as a primary means for effecting hemostasis, without prior suturing or other closure procedures. It would be even further desirable if such methods and devices could also be used for advancing and tightening suture knots which are formed directly over the adventitial surface of the blood vessel wall.

2. Description of the Background Art

A device and method for placing an inflatable balloon over a vascular puncture site and applying laser energy to thermally weld the artery are described in U.S. Pat. No. 4,929,246. Hemostatic closure devices which place a collagen plug and polymer anchor on the adventitial and luminal surfaces of a blood vessel at a puncture site are described in a brochure of the Kensey Nash Corporation entitled *The Hemostatic Puncture Close Device* (undated). Vessel closure devices employing collagen and other plugs are described in U.S. Pat. Nos. 5,222,974; 5,192,302; 5,108,421; 5,061,274; 5,021,059; 4,890,612; and 4,744,364. A three part hemostasis device for introducing a collagen plug over a vascular puncture site is described in Merino et al., *A Vascular Hemostasis Device for Percutaneous Interventional Procedures*, Mount Sinai Medical Center, New York, N.Y. (undated) and Ernst et al., *Immediate Sealing of Arterial Puncture Sites after Catheterization and PTCA Using a Vascular Hemostasis Device With Collagen: An International Registry*, (undated). Knot pushers, appliers, and related suturing devices are described in U.S. Pat. Nos. 5,176,691; 5,201,744; 5,250,054; 4,803,984; 2,595,086; 2,131,321; 1,940,351; and 1,574,362.

Co-pending applications having U.S. application Ser. Nos. 07/989,611, 08/148,089, and PCT/US93/11864, describe methods and apparatus for suturing vascular punctures.

SUMMARY OF THE INVENTION

The present invention provides methods and devices for engaging and applying pressure directly to the adventitial surface of a blood vessel wall in the region of a vascular puncture in order to effect or enhance hemostasis. The adventitial surface is the outer most covering of the blood vessel, also referred to as the tunica adventitia in the case of arteries. By "direct" application of pressure, it is meant that a surface or other pressure-applying means is contacted directly against the adventitial surface at the distal end of a percutaneous tissue tract which has been formed as part of the vascular puncture. As explained above, most prior methods for effecting hemostasis relied on the indirect application of pressure to the puncture site by manually pressing or clamping the patient's skin over the vascular puncture. Application of pressure to the skin and subcutaneous tissue overlying the puncture is less effective in providing hemostasis, more uncomfortable to the patient, and has the other problems discussed above. Moreover, it has been found that the direct application of pressure can achieve hemostasis without the need to apply heat, as has been proposed by others.

The present invention preferably relies on contacting an annular surface, usually a flat or slightly convex surface having a circular or elliptical periphery, over suture and/or a guidewire extending from the puncture through the tissue tract and directly against the adventitial surface of the blood vessel wall. In a first aspect of the present invention, the surface can by itself provide hemostasis sufficient to permit clotting and the initial stages of healing of the vascular puncture. For example, the annular surface can be introduced over the guide wire which is left in place until the patient's condition appears to have stabilized sufficiently to withdraw the guide wire and subsequently the annular surface. It has been found that the direct application of pressure with the annular surface allows clotting and provides hemostasis even without the application of heat, as proposed in U.S. Pat. No. 4,929,246.

In another aspect, the method of the present invention is used in combination with other procedures for providing hemostasis. In a first particular embodiment, the method provides for contacting the annular surface against a vascular puncture site which has been previously sutured to effect primary closure. Preferably, the annular surface will be introduced over the free ends of the suture in order to inhibit or stop residual bleeding which might occur in rare cases even after the primary suture loop(s) have been tied and tightened. The annular surface can also be used in conjunction with the application of tissue glues, such as those including fibrinogen, thrombin, and the like. In all cases, it is possible to secure the surface within the tissue tract so that manual retention of the surface is not necessary.

The method of the present invention will apply sufficient force over a predetermined area (i.e., pressure) to effect hemostasis at the vascular puncture site. Preferably, a force in the range from about 5 g to 50 g will be applied over an area in the range from about 6 mm$^2$ to 30 mm$^2$. The resulting pressures are typically applied for a period from about 10 minutes to 24 hours in order to effect hemostasis.

A device according to the present invention comprises a shaft having a proximal end, a distal end, and an annular surface at its distal end. The surface will generally have a circular or elliptical periphery and will span an area in the range from 6 mm$^2$ to 30 mm$^2$. The surface will be oriented at an angle from about 30° to 60° relative to the axis of the shaft. It will be appreciated that the tissue tract into the femoral artery formed by the Seldinger technique typically lies at an angle from about 30° to 60° relative to the arterial axis. The angle of the annular surface relative to the shaft is thus selected to permit introduction of the shaft through the tissue tract and positioning of the annular surface so that it lies flat over the adventitial surface of the blood vessel wall.

In a preferred aspect of the device, an axial channel or lumen is provided in the shaft to receive the suture or guide wire and facilitate anchoring the suture or guidewire to the proximal end of the device to hold the device in place.

In an optional aspect of the present invention, a pair of circumferentially spaced-apart apertures or slots are formed at the edges of the annular surface or a proximal surface to receive free suture ends for use of the device on punctures which have been previously sutured. The apertures or slots permit the device to be used as a knot pusher for advancing and tightening knots which are tied outside the tissue tract.

In the exemplary device, the shaft is cylinder and the annular surface is formed as a planar section through the cylinder at the preferred angle. The cylinder typically has a diameter from 2 mm to 10 mm and a length from about 7 cm to 12 cm.

BRIEF DESCRIPTION OF THE DRAWINGS

FIG. 1 is a perspective view of a blood vessel puncture occlusion device constructed in accordance with the principles of the present invention.

FIG. 2 is a perspective view of the device of FIG. 1, taken from a bottom perspective.

FIG. 3 is a top plan view of the device of FIG. 1.

FIG. 4 is a side cross-sectional view of the device of FIG. 2.

FIG. 5 illustrates a simplified device constructed in accordance with the principles of the present invention.

FIG. 6 is a right end view of the device of FIG. 5.

FIGS. 17 and 18 illustrate a third method for providing hemostasis according to the present invention, where a suture loop is first formed and closed, and pressure applied over free ends of the suture extending from the vascular puncture site.

DESCRIPTION OF THE SPECIFIC EMBODIMENTS

Figure 7:
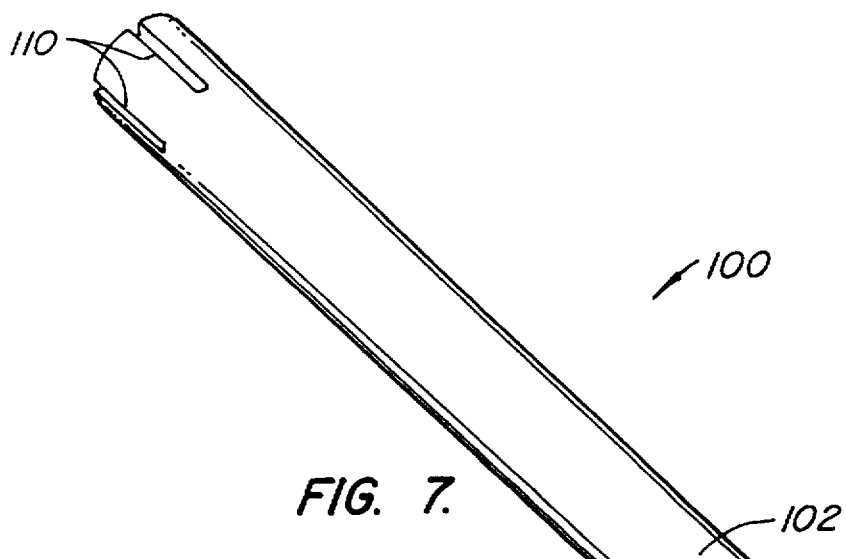
FIG. 7 is a perspective view of an alternative embodiment of the blood vessel puncture occlusion device of the present invention.
Figure 8:
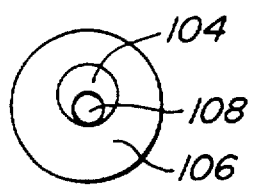
FIG. 8 is a distal end view of the device of FIG. 7.
Figure 9:
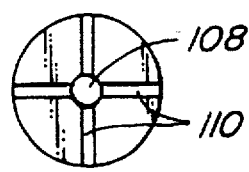
FIG. 9 is a proximal end view of the device of FIG. 7.
Figure 10:
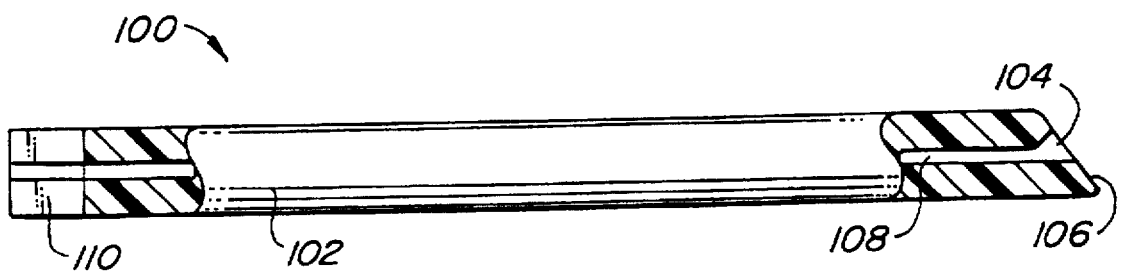
FIG. 10 is a side view of the device of FIG. 7 shown in partial section.

Referring now to FIGS. 1–4, a blood vessel puncture occlusion device 10 incorporating each of the features described in the above invention summary will be described. The device 10 comprises an elongate shaft 12 having a proximal end 14 and an annular surface 16 at its distal end 18. An aperture or port 20 is formed generally in the center of the annular surface 16 and extends to an opening 22 (FIGS. 3 and 4) at the distal end of an axial channel 24. A pair of circumferentially spaced-apart apertures or slots 26 are formed on opposite sides of the annular surface 16. An O-ring 28 circumscribes the shaft 12 near its proximal end 14 and serves to clamp or anchor suture or a guide wire which is brought through slots 26 or opening 22 into channel 24, as will be described in more detail hereinafter.

The annular surface 16 in the exemplary device 10 comprises a planar section of a cylindrical body which forms the shaft 12. The surface 16 is generally flat and formed at an angle in the range from 30° to 60° relative to the axis of shaft 12, preferably from 40° to 50°. The annular surface 16 need not be completely flat, and may in some cases be slightly convex in order to focus or center applied pressure to the puncture site in the blood vessel wall. Typically, the annular surface 16 will have an area in the range from 6 mm$^2$ to 30 mm$^2$, preferably from 15 mm$^2$ to 25 mm$^2$. In the case of convex surfaces, the center of the surface will typically be raised from the edge by distance in the range from about 0.1 mm to 1 mm. The length of the shaft 12 will typically be in the range from 7 cm to 12 cm. The cylindrical shaft 12 will usually have a uniformed diameter in the range from 2 mm to 10 mm, preferably from 6 mm to 8 mm. The occlusive surface 16 which results is thus an elliptical surface which is a section through the cylindrical shaft.

The surface 16 may be compliant or non-compliant. By "non-compliant" it is meant that the surface 16 will be able to apply pressure to the vascular puncture site without significant yield. In the embodiment of FIGS. 1-4, the surface 16 is non-compliant since it is a terminal surface of solid cylindrical shaft 12, typically composed of a rigid material, such as polycarbonate, glass, ceramic, metal, or the like. In other cases, it would be possible to form the surface 16 from a compliant material, such as an elastomeric polymer, e.g., silicone rubber.

A variety of mechanisms could be provided for securing suture or a guide wire to the proximal end of the device 10. In addition to O-ring 28 which is illustrated, suitable mechanisms include clips, adhesives, tapes, cleats, slits, latches, hooks, and other structures for securing or tying suture or a guide wire to the proximal end.

Referring now to FIGS. 5 and 6, an alternative embodiment 30 of the device of the present invention is illustrated. Device 30 is simplified (in comparison to the device of FIGS. 1-4) and comprises an elongate rod 32 having a finger-grasping means 34 at its proximal end and a pressure-applying surface 36 at its distal end. The surface is a circular disc, typically formed from metal, plastic, glass, ceramic, or the like, having a diameter in the range from 2 mm to 10 mm, preferably from 6 mm to 8 mm. The surface 36 will be oriented at an angle Θ in the range from 30° to 60°, preferably from 40° to 50°. The length of rod 32 will typically be in the range from 7 cm to 12 cm, preferably from 8 cm to 10 cm. For use in at least some of the methods of the present invention, there is no need to provide for apertures or slots for receiving a guide wire and/or free suture ends as described in more detail hereinafter.

An alternative embodiment 100 of a blood vessel puncture occlusion device of the present invention is illustrated in FIGS. 7-10. The device 100 is intended for applying pressure against the adventitial surface of a blood vessel wall surrounding a puncture site and will not be suitable for knot advancement. The device 100 comprises a shaft 102 having the dimensions generally set forth above for the embodiment of FIGS. 1-4, but will be composed of a relative soft, compliant material, such as silicone rubber. An opening or gap 104 will be formed in the distal surface 106 which engages the adventitial surface of the blood vessel wall. The opening has a width and depth sufficient to receive a knot in suture, typically from 1 mm to 3 mm and 1 mm to 5 mm, respectively, and permits additional tightening or cinching on a knot in suture, where the knot is received in the opening 104 and suture passes proximally through axial lumen 108. The ability to tighten the suture is particularly valuable when the knot has not been tied closely over the adventitial surface, i.e., an "air knot" has been inadvertently tied. The device 100 further includes slots 110 formed at the proximal end. The slots 110 facilitate tying of suture to the device to hold the device in place for extended time periods.

The device 100 will also be suitable for application of force to provide hemostasis, even when suture has not been previously placed. The device 100 can be introduced over a guidewire which passes through the tissue tract and into the blood vessel or lumen, and pressure applied until hemostasis is achieved or another procedure initiated to achieve hemostasis.

Figure 11:
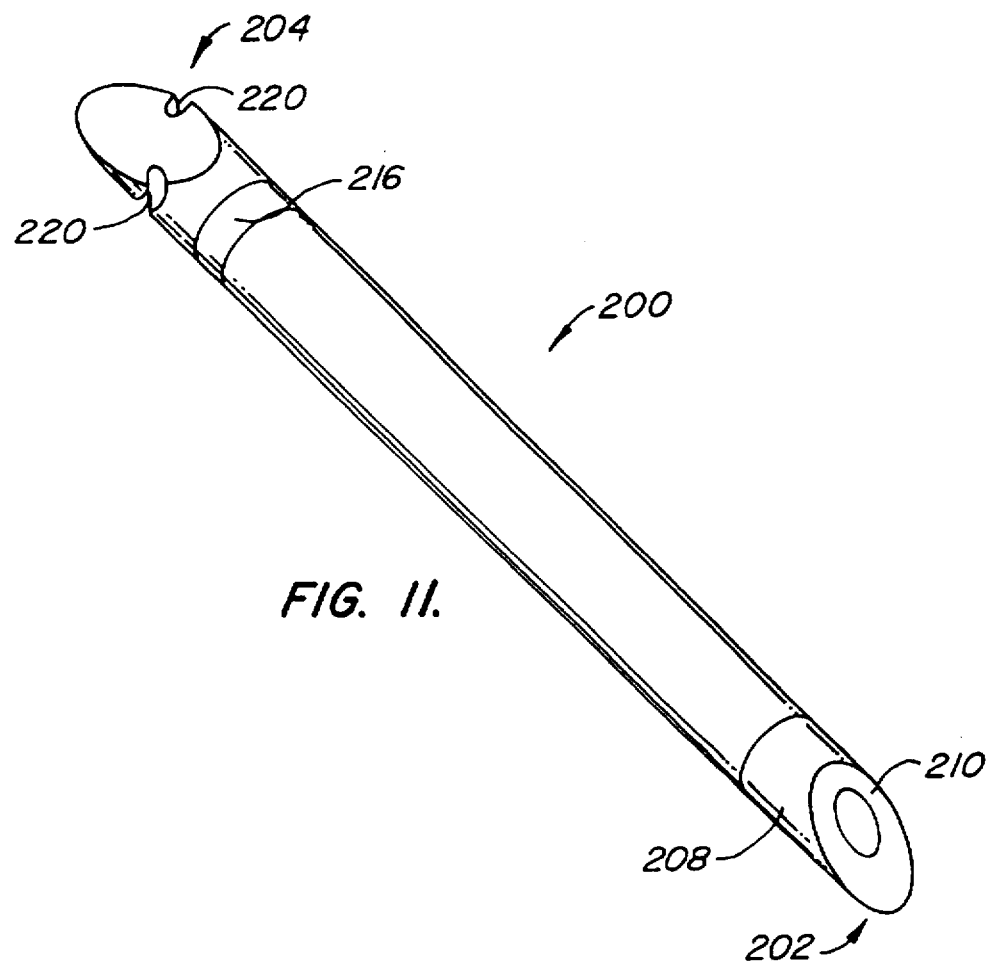
FIG. 11 is a perspective view of another alternative embodiment of the blood vessel puncture occlusion device of the present invention.
Figure 12:
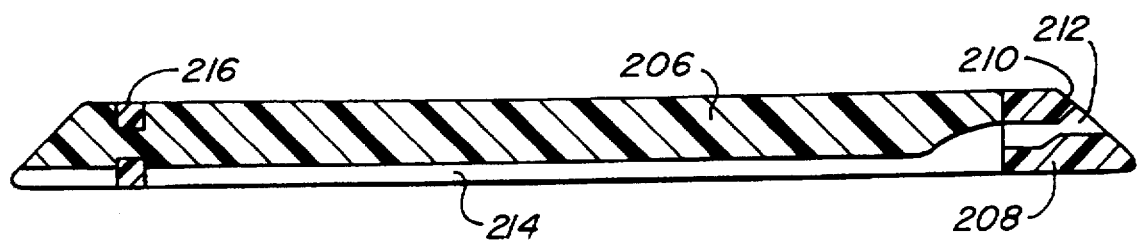
FIG. 12 is a side view of the device of FIG. 11 shown in partial section.

Another alternative embodiment 200 of the blood vessel puncture occlusion device of the present invention is illustrated in FIGS. 11 and 12. The device 200 has a first end 202 intended for applying pressure over a vascular penetration to achieve hemostasis, as generally described for previous embodiments, and a second end 204 intended for advancing knots or knot throws, also as generally described for previous embodiments.

The device 200 includes a cylindrical shaft or body 206 which is typically formed from a relative hard or rigid material, such as polycarbonate. A soft tip 208 is at the first end 202 and defines a compliant surface 210 for engaging the adventitial surface of the blood vessel. An opening or gap 212 is formed in the soft tip 208 and is connected to an axial channel 214 in the shaft 206, and an O-ring 216 is provided to anchor the device in place. Suture and/or a guidewire can be received through the opening 212 and into the channel 214 to achieve or enhance hemostasis as generally described above for the other embodiments.

Slots 220 are formed at the second end 204 to receive free suture ends and permit knot advancement. In this way, the user can select which end of the device 200 to use depending on whether hemostasis or knot advancement is the primary objective.

Figure 13:
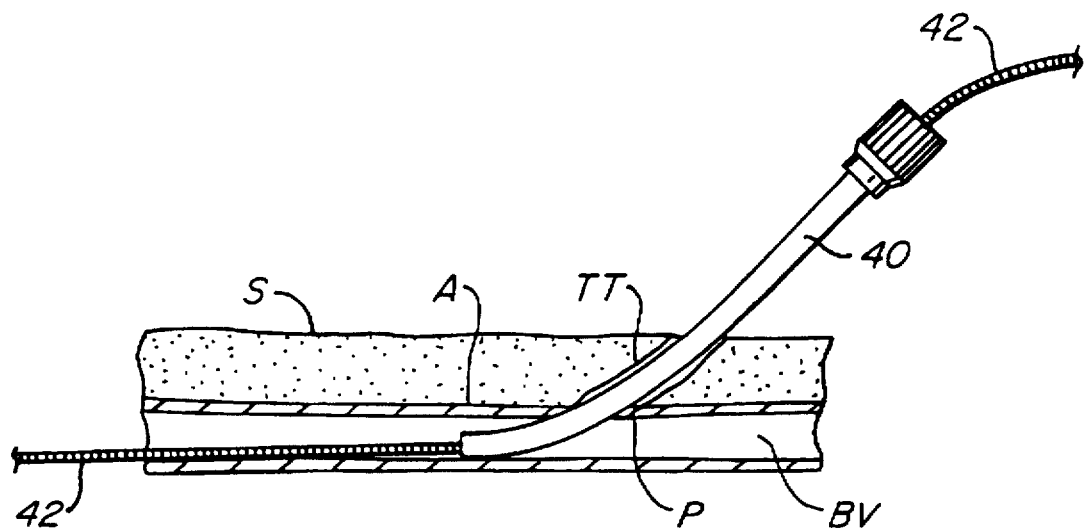
FIG. 13 illustrates an introducer sheath and guide wire which have been placed through a vascular puncture in a blood vessel by the Seldinger technique.
Figure 14:
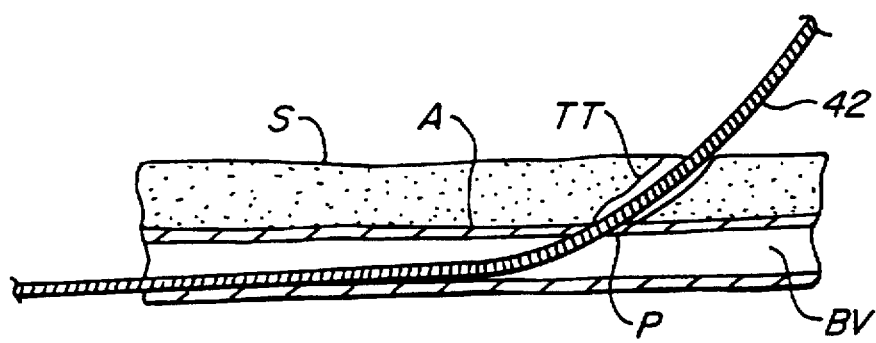
FIG. 14 illustrates the vascular puncture as in FIG. 7 after the introducer sheath has been withdrawn.

Referring now to FIGS. 13 and 14, an introducer sheath 40 and guide wire 42 may be introduced to a blood vessel lumen BV through a tissue tract TT. The tissue tract TT extends percutaneously from the outer surface of the patient's skin S to a vascular puncture P formed through the blood vessel wall. The adventitial surface A is the exterior surface of the blood vessel wall.

The introducer sheath 40 and guide wire 42 may be used in a variety of conventional diagnostic and interventional procedures in a manner well known in the art. At the end of such procedure(s), it will be necessary to close and seal the vascular puncture P. According to the method of the present invention, the introducer sheath 40 will be partially or totally withdrawn, as illustrated in FIG. 14, leaving the tissue tract TT and puncture P open. It will be appreciated that the open tissue tract TT and puncture P can result in substantial blood loss after the introducer 40 has been withdrawn.

Figure 15:
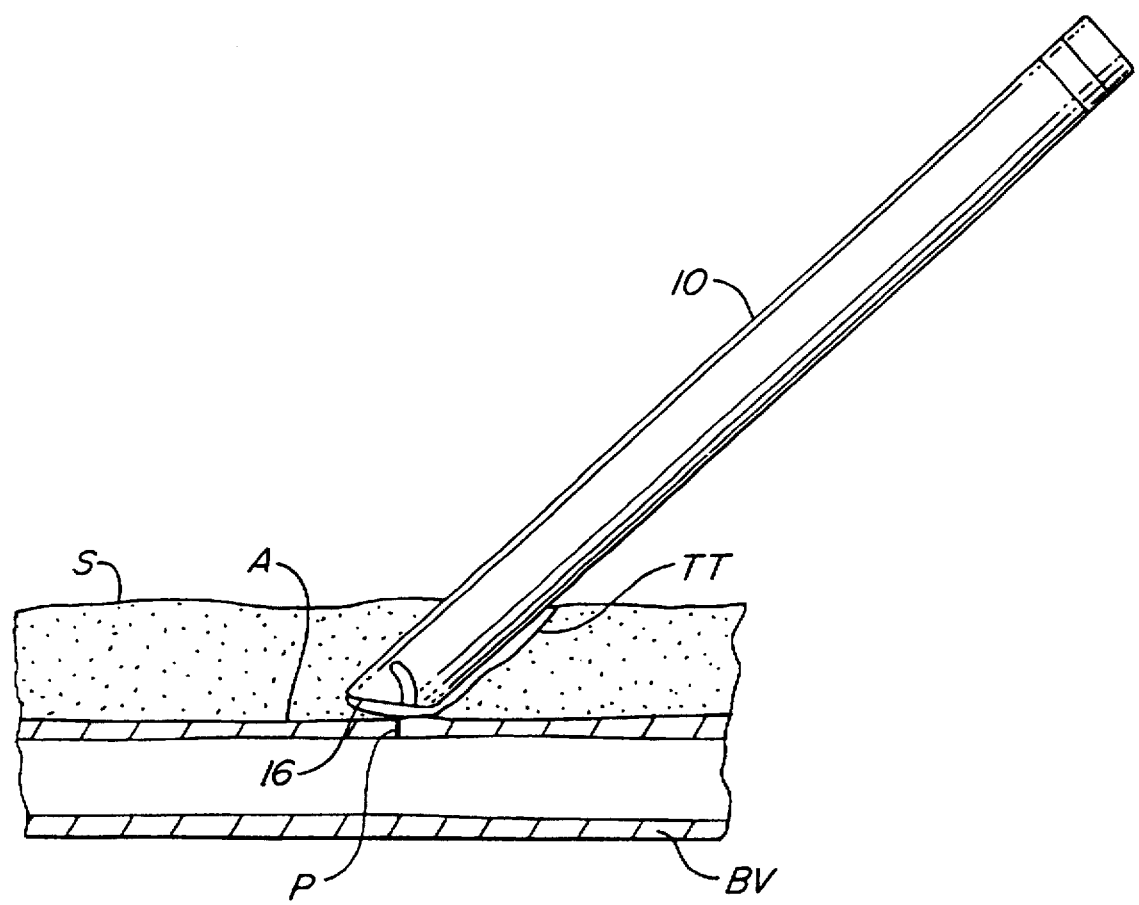
FIG. 15 illustrates a first method for providing hemostasis according to the present invention where pressure is applied directly in the absence of suture and a guide wire.

According to a first aspect of the method of the present invention, blood loss through the puncture P and tissue tract TT can be staunched by removing with guide wire 42 and introducing the device 10 through the tissue tract so that the annular surface 16 directly engages the adventitial wall A over the puncture P, as illustrated in FIG. 15. The non-compliant surface will be engaged against the adventitial surface A with a force typically in the range from 5 g to 50 g, more typically from 5 g to 25 g. Pressure may be maintained for time sufficient to permit initial blood coagulation and healing of the puncture site P. It will be appreciated that such direct application of pressure, without suturing or other means of primary closure, will generally only be useful for relatively small punctures, and for patients who have undergone little or no anti-coagulation treatment.

Figure 16:
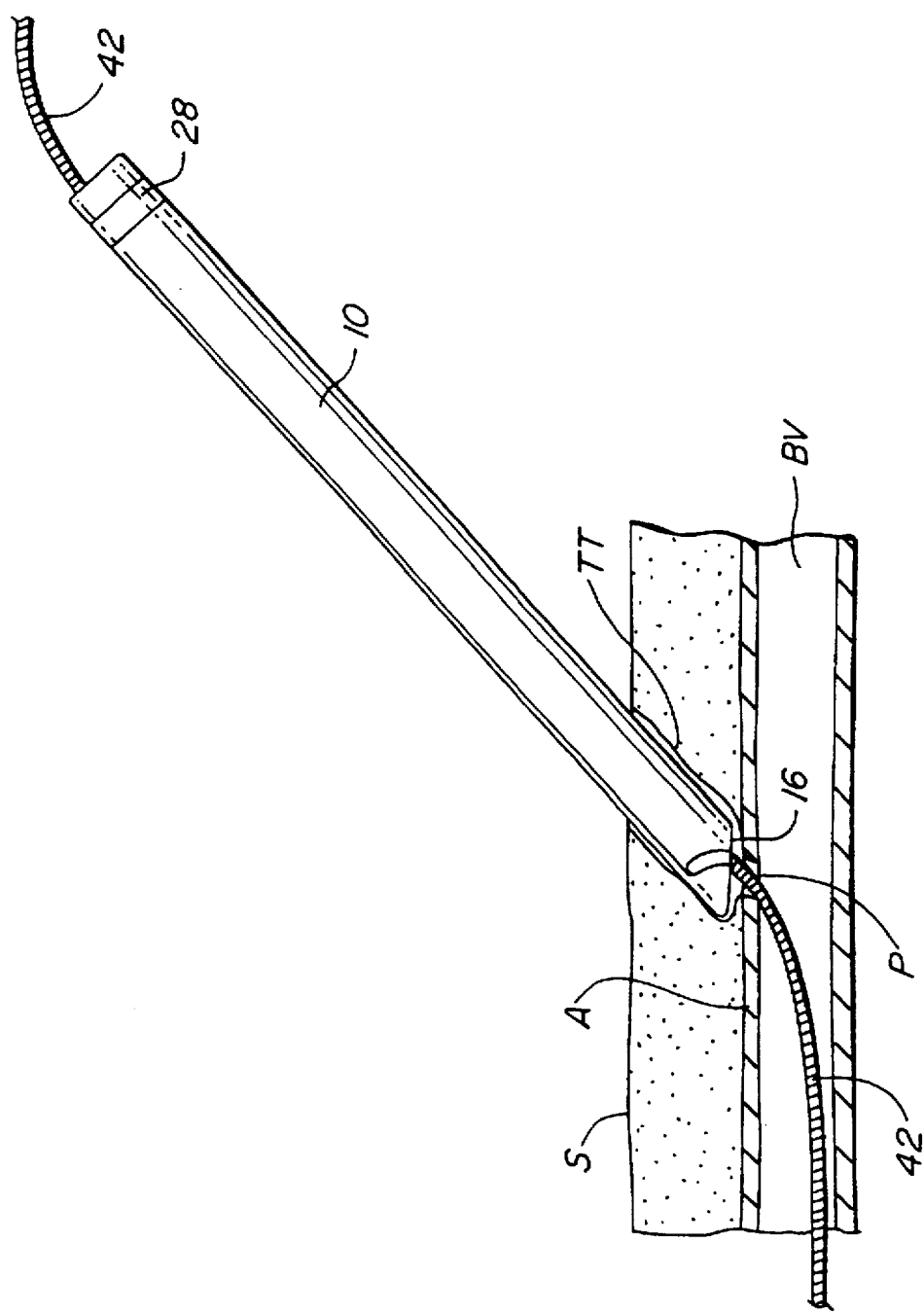
FIG. 16 illustrates a second method for providing hemostasis according to the present invention where pressure is applied over a guide wire.

In a second aspect of the method of the present invention, as illustrated in FIG. 16, the guide wire 42 may be left in place with the device 10 introduced thereover. The guide wire 42 will pass through aperture 20 in the non-compliant surface 16, and upward through the channel 24. The applied force and treatment time will generally be as described above. The device 10 may optionally be held in place by securing the guide wire with O-ring 28, or with any other securing structure which may be provided on the device 10. It will be appreciated that the guide wire 10 has a very small diameter, typically being about 0.038 inches, and that hemostasis and clotting may initiate around the guide wire, with the guide wire 42 being subsequently withdrawn. In some case, the guide wire may be withdrawn with the device 10 remaining in place with non-compliant surface 16 engaged against the puncture P.

Referring now to FIGS. 17–18, a preferred method according to the present invention will be described. A primary closure of puncture P will be effected by passing a suture loop L through the blood vessel wall on opposite side of the puncture. The suture loop L is then tied-off, or otherwise secured, and the knot or other fastening structure passed down through the tissue tract to lie over the adventitial surface A. Methods and devices for forming such suture loops are well described in co-pending applications Ser. No. 07/989,611, Ser. No. 08/148,089, and PCT/US93/11864, the disclosures of which are incorporated herein by reference.

Once the loop L has been formed, a first knot K, typically a square knot, may be pushed down the tissue tract TT using a rod or other conventional knot pusher. A particularly useful not pusher is described in copending application Ser. No. [08/552,211, (attorney docket no. 15508-14], the disclosure of which is incorporated here in by reference). Additional knot throws may be advanced using the device 10 by passing each of the two free suture ends through one of the slots 26 and outward through the channel 24 (FIGS. 1–4). The additional knot throws are thus advanced and tightened by tensioning the free suture ends and pushing the non-compliant surface 16 against the suture loop. The non-compliant surface 16 will at the same time apply pressure over the puncture in adventitial wall A to inhibit hemostasis. Advice 10 may be secured by fastening the free suture ends using O-ring 28, with the device 10 being left in place for a desired amount of time to promote hemostasis and initial clot formation.

It will be further appreciated that the device 10 can be used wherever it is desired to apply direct pressure to a vascular puncture through a tissue tract. It can be used, for example, if other methods for closing a vascular puncture have failed. The device can also be used in conjunction with the application of "tissue glues" at the site of the vascular puncture. Suitable tissue glues will comprise one or more components of the clotting cascade, typically comprising at least fibrinogen or thrombin, and more typically comprising both fibrinogen and thrombin. Suitable tissue glues are well described in the patent and medical literature. See, for example, U.S. Pat. Nos. 4,928,603; 4,909,251; 4,427,650, the disclosures are incorporated herein by reference. The tissue glues may be introduced prior to application of pressure using the device 10 or maybe coated on the non-compliant surface and delivered to the site of vascular puncture using the device 10.

Although the foregoing invention has been described in some detail by way of illustration and example, for purposes of clarity of understanding, it will be obvious that certain changes and modifications may be practiced within the scope of the appended claims.

What is claimed is:

1. A method for occluding a puncture of a blood vessel at the end of a tissue tract, said method comprising:

applying pressure without applying heat directly to an adventitial surface of the blood vessel with a surface which is engaged against the adventitial surface, wherein a force in the range from 5 g to 50 g is applied over an area in the range from about 6 mm$^2$ to 30 mm$^2$ for a time in the range from about 10 minutes to 24 hours, the pressure applied at least in part by tensioning a member, the member selected from the group consisting of suture and a guidewire, and anchoring the member to a shaft which extends out the tissue tract from the surface, the force being transferred along the shaft and to the surface from outside the tissue tract; and removing the shaft with the surface through the tissue tract after applying the pressure.

2. A method as in claim 1, wherein the pressure is applied with an annular flat surface which is engaged against the adventitial surface.

3. A method as in claim 2, wherein the annular surface is introduced over the member, the member passing through the adventitial surface and extending through the tissue tract.

4. A method as in claim 1, further comprising applying a tissue glue at the puncture while applying pressure.

5. A method as in claim 4, wherein the applying tissue glue step comprises applying at least one member of the clotting cascade selected from the group consisting of fibrinogen and thrombin.

6. A method as in claim 1, further comprising focussing the pressure at the puncture, the pressure being applied with a convex surface having a center raised in the range from 0.1 mm to 1 mm relative to an edge.

7. A method as claimed in claim 1, wherein the member is not attached to a fastener within a lumen of the blood vessel.

8. A method for occluding a puncture of a blood vessel at the end of a tissue tract, said method comprising:

contacting an annular surface against the adventitial surface of the blood vessel over the puncture with sufficient pressure to substantially inhibit blood flow through the puncture, the surface defining an opening through which suture extends, the suture forming a suture loop which passes through the adventitial surface to attach the suture loop to the blood vessel, wherein the suture is not attached to a fastener within a lumen of the blood vessel, the surface contacting the adventitial surface surrounding the suture loop, wherein the surface is a distal end of a shaft, wherein said shaft and said surface form an angle which is substantially equal to an angle of the tissue tract relative to the adventitial surface so that the surface lies substantially flat over the adventitial surface while pressure is being applied, and wherein a force in the range from 5 g to 50 g is applied over an area in the range from about 6 mm$^2$ to 30 mm$^2$ for a time in the range from about 10 minutes to 24 hours; and removing the shaft with the surface through the tissue tract after contacting the adventitial surface with the surface for the time.

9. A method as in claim 8, further comprising applying a tissue glue at the puncture while applying pressure.

10. A method as in claim 9, wherein the applying tissue glue step comprises applying at least one member of the clotting cascade selected from the group consisting of fibrinogen and thrombin.

11. A method as in claim 8, further comprising focussing the pressure at the puncture, the surface being elliptical and convex, having a center raised in the range from 0.1 mm to 1 mm relative to an edge.

12. A method for occluding a puncture of a blood vessel at the end of a tissue tract, said method comprising:

providing an occlusion device having a shaft defining a proximal end and a distal end, the shaft forming an angle in the range from about 30° to 60° with a surface at its distal end, wherein said angle is substantially equal to an angle of the tissue tract relative to an adventitial surface of the blood vessel, and wherein the surface includes an opening defined by a hole or a slot;

manually grasping the proximal end of the device, inserting a suture into the opening, passing the distal end through the tissue tract over the suture, and contacting the surface generally flat directly against the adventitial surface of the blood vessel over the puncture with sufficient pressure to substantially inhibit blood flow through the puncture; and removing the shaft and the surface through the tissue tract.

13. A method as in claim 12, wherein a force in the range from 5 g to 50 g is applied over an area in the range from about 6 mm$^2$ to 30 mm$^2$ for a time in the range from about 10 minutes to 24 hours.

14. A method as in claim 12, further comprising securing the device within the tissue tract so that said sufficient pressure is applied without manual grasping.

15. A method as in claim 12, further comprising applying a tissue glue at the puncture while applying pressure.

16. A method as in claim 15, wherein the applying tissue glue step comprises applying at least one member of the clotting cascade selected from the group consisting of fibrinogen and thrombin.

17. A method as in claim 12, further comprising focussing the pressure at the puncture, the surface being elliptical and convex, having a center raised in the range from 0.1 mm to 1 mm relative to an edge.

18. A method for closing a puncture of a blood vessel at the distal end of a tissue tract, said method comprising:

forming a suture loop which passes through a blood vessel wall on opposite sides of the puncture beyond the puncture with free ends of the suture passing out through the tissue tract;

tightening and securing the free ends of the suture to close the puncture;

introducing a surface through the tissue tract over the tightened and secured suture ends;

applying sufficient pressure directly to an adventitial surface of the blood vessel with the surface to inhibit blood leakage through the sutured puncture; and removing the surface through the tissue tract.

19. A method as in claim 18, wherein a force in the range from 5 g to 50 g is applied over an area in the range from about 6 mm$^2$ to 30 mm$^2$ for a time in the range from about 10 minutes to 24 hours.

20. A method as in claim 18, further comprising securing the surface within the tissue tract so that said sufficient pressure is applied without manual grasping.

21. A method as in claim 20, wherein the surface comprises the distal end of a shaft which further defines a proximal end, wherein the introducing step comprises passing the free ends of the suture through an opening in the surface into a lumen of the shaft and out a proximal opening in the shaft, and further comprising tensioning the free ends of the suture and fixing the free ends of the tensioned suture to the shaft proximal of the tissue tract so that the shaft is loaded in compression.

22. A method as claimed in claim 21, wherein the fixing of the free ends of the suture to the shaft comprises tying the suture ends to slots cut in the proximal end of the shaft.

23. A method as in claim 21, wherein the fixing of the free ends of the suture to the shaft comprises disposing the free ends of the suture between an O-ring and the shaft.

24. A method as in claim 21, wherein the surface is compliant.

25. A method as in claim 18, further comprising applying a tissue glue at the puncture while applying pressure.

26. A method as in claim 25, wherein the applying tissue glue step comprises applying at least one member selected from the group containing fibrinogen and thrombin.

27. A method as claimed in claim 18, wherein the surface comprises the distal end of a shaft which further defines a proximal end, and wherein the suture securing step comprises advancing a knot distally along the free ends of the suture using a pair of circumferentially spaced apart slots on one end of the shaft.

28. A method as in claim 27, further comprising securing the surface within the tissue tract so that said sufficient pressure is applied without manual grasping by fixing the free ends of the suture to the shaft proximal of the tissue tract.

29. A method as claimed in claim 18, wherein the suture is not attached to a fastener within a lumen of the blood vessel.

30. A method for occluding a puncture of a blood vessel at the end of a tissue tract, said method comprising:

providing an occlusion device having a shaft defining a proximal end and a distal end, the shaft including a hole or a slot defining an opening in a surface at the distal end;

introducing a guidewire through the puncture;

inserting the guidewire into the opening;

passing the surface through the tissue tract over the guidewire;

contacting the surface generally flat against the adventitial surface of the blood vessel over the puncture with sufficient pressure to substantially inhibit blood flow through the puncture; and anchoring the guidewire to the shaft proximally of the tissue tract so that the shaft is held in place for a time between 10 minutes and 24 hours.

31. A method for occluding a puncture of a blood vessel at the end of a tissue tract, the method comprising:

passing suture through an adventitial surface of the blood vessel beyond the puncture to form a suture loop which is attached to the blood vessel and which helps close the puncture;

introducing an end of the suture into a hole or a slot of a surface, the surface being at a distal end of a shaft;

inserting the shaft with the surface through the tissue tract;

contacting the surface directly against the adventitial surface of the blood vessel over the sutured puncture with sufficient pressure and for sufficient time to substantially inhibit blood flow through the sutured puncture; and removing the shaft with the surface through the tissue tract.

32. A method as claimed in claim 31, wherein the suture is not attached to a fastener within a lumen of the blood vessel.

* * * * *